United States Patent
Yang et al.

(10) Patent No.: US 11,186,533 B2
(45) Date of Patent: *Nov. 30, 2021

(54) CHALCONE COMPOUND AND PREPARATION METHOD THEREOF

(71) Applicant: SOUTH CHINA BOTANICAL GARDEN, CHINESE ACADEMY OF SCIENCES, Guangzhou (CN)

(72) Inventors: Bao Yang, Guangzhou (CN); Yueming Jiang, Guangzhou (CN)

(73) Assignee: SOUTH CHINA BOTANICAL GARDEN, CHINESE ACADEMY OF SCIENCES, Guangzhou (CN)

( * ) Notice: Subject to any disclaimer, the term of this patent is extended or adjusted under 35 U.S.C. 154(b) by 179 days.

This patent is subject to a terminal disclaimer.

(21) Appl. No.: 16/626,906

(22) PCT Filed: Sep. 21, 2018

(86) PCT No.: PCT/CN2018/106841
§ 371 (c)(1),
(2) Date: Dec. 27, 2019

(87) PCT Pub. No.: WO2020/042250
PCT Pub. Date: Mar. 5, 2020

(65) Prior Publication Data
US 2021/0331995 A1    Oct. 28, 2021

(30) Foreign Application Priority Data

Aug. 30, 2018 (CN) .......................... 201811003986.2

(51) Int. Cl.
*C07C 45/80* (2006.01)
*C07C 49/835* (2006.01)
*A61Q 19/00* (2006.01)
*C07C 45/81* (2006.01)
*A61K 8/35* (2006.01)

(52) U.S. Cl.
CPC .............. *C07C 49/835* (2013.01); *A61K 8/35* (2013.01); *A61Q 19/00* (2013.01); *C07C 45/80* (2013.01); *C07C 45/81* (2013.01); *C07C 2601/16* (2017.05)

(58) Field of Classification Search
CPC ........................... C07C 45/50; C07C 2601/16
See application file for complete search history.

(56) References Cited

PUBLICATIONS

He Xuemei, et al., A Review on Chemical Constituents and Pharmacological Activity of *Morus* Species, Science of Sericulture, Dec. 31, 2014, pp. 328-338, vol. 40, No. 2.

Ji Yeon Jeong, et al., Pancreatic Lipase Inhibitory Constituents From Morus Alba Leaves and Optimization for Extraction Conditions, Bioorganic & Medicinal Chemistry Letters, Apr. 22, 2015, pp. 2269-2274, vol. 25, No. 11.

Ji Yeon Jeong, et al., Characterization of Melanogenesis Inhibitory Constituents of Morus Alba Leaves and Optimization of Extraction Conditions Using Response Surface Methodology, Molecules, May 14, 2015, pp. 3730-8741, vol. 20, No. 15.

*Primary Examiner* — Sikarl A Witherspoon
(74) *Attorney, Agent, or Firm* — Bayramoglu Law Offices LLC

(57) ABSTRACT

A method for preparing 2,2',4,4'-Tetrahydroxy-3-(2"-hydroxy-3"-methylbutyl-3"-alkenyl)chalcone includes the following steps: subjecting a *Morus alba* leaf to extraction with an aqueous solution of methanol or ethanol having a volume fraction of 40%-100%, concentrating an extract to remove methanol or ethanol and dissolving in water, subjecting to extraction with petroleum ether and ethyl acetate successively, and concentrating an ethyl acetate extract to obtain a paste; chromatographing the paste over a silica gel column using chloroform-methanol, collecting an eluate where the volume ratio of chloroform-methanol is 95/5; chromatographing the eluate over a reversed-phase column using methanol-water, collecting an eluate where the volume ratio of methanol-water is 60/40, and thereby the compound is obtained.

6 Claims, No Drawings

CHALCONE COMPOUND AND PREPARATION METHOD THEREOF

CROSS REFERENCE TO RELATED APPLICATIONS

This application is the national phase entry of International Application No. PCT/CN2018/106841, filed on Sep. 21, 2018, which is based upon and claims priority to Chinese Patent Application No. 201811003986.2, filed on Aug. 30, 2018, the entire contents of which are incorporated herein by reference.

TECHNICAL FIELD

The present invention relates to the field of natural product chemistry, and particularly relates to a chalcone compound and a preparation method thereof.

BACKGROUND

Morus alba is an evergreen macrophanerophyte in the family Moraceae, widely planted in tropical and subtropical regions. Morus alba fruits are sweet and delicious, with high nutritional value and health-care functions, have the effects of treating canities and anti-inflammatory, and thus are well received by consumers. Morus alba leaves, identified as a new vegetable food material, have a fresh taste and have gradually been accepted by consumers. Studies have found that Morus alba leaves are rich in flavonoids and have biological activities such as anti-oxidation, anti-cancer and immunoregulation. However, there are few studies on the active ingredients of Morus alba leaves, and the composition of related active substances remains to be studied.

SUMMARY

One object of the present invention is to provide a preparation method of a chalcone compound, and in particular, a preparation method of 2,2',4,4'-tetrahydroxy-3-(2"-hydroxy-3"-methylbutyl-3"-alkenyl)chalcone.

The compound of the present invention, 2,2',4,4'-tetrahydroxy-3-(2"-hydroxy-3"-methylbutyl-3"-alkenyl)chalcone, is isolated from a Morus alba leaf, and has a structure according to formula (I):

formula (I)

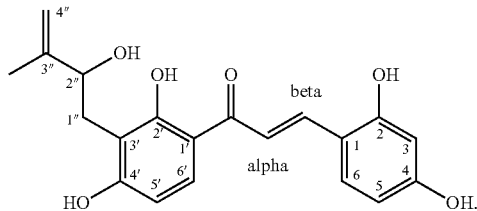

A preparation method of the 2,2',4,4'-tetrahydroxy-3-(2"-hydroxy-3"-methylbutyl-3"-alkenyl)chalcone, comprises the following steps:

subjecting a Morus alba leaf to extraction with an aqueous solution of methanol or ethanol having a volume fraction of 40%-100%, concentrating an extract to remove methanol or ethanol and dissolving in water, subjecting to extraction with petroleum ether and ethyl acetate successively, and concentrating an ethyl acetate extract to obtain a paste; chromatographing the paste over a silica gel column by gradient elution using chloroform-methanol with a volume ratio of 100/0 to 60/40, collecting an eluate where the volume ratio of chloroform-methanol is 95/5; chromatographing the eluate over a reversed-phase column by gradient elution using methanol-water with a volume ratio of 10/90 to 100/0, collecting an eluate where the volume ratio of methanol-water is 60/40, and thereby the 2,2',4,4'-tetrahydroxy-3-(2"-hydroxy-3"-methylbutyl-3"-alkenyl)chalcone is obtained.

The Morus alba leaf is provided as Morus alba leaf powders, which are obtained by drying a fresh Morus alba leaf and pulverizing into powders.

In the step of subjecting the Morus alba leaf to extraction with the aqueous solution of methanol or ethanol having the volume fraction of 40%-100%, the aqueous solution of methanol or ethanol is used according to a proportion of 5 to 20 mL/g Morus alba leaf (i.e., 5 to 20 mL of the aqueous solution of methanol or ethanol is used for one gram of the Morus alba leaf), an extraction temperature is 25° C. to 80° C., and an extraction time is 1 to 72 hours.

In the step of concentrating the extract to remove methanol or ethanol and dissolving in water, the extract is concentrated at 40° C. to 80° C. to remove methanol or ethanol, and dissolved by adding water wherein a volume of the water is 1 to 5 times that of the concentrated extract.

The step of subjecting to extraction with petroleum ether and ethyl acetate successively, comprises first extracting with petroleum ether for 3 to 12 times and then extracting with ethyl acetate for 3 to 12 times.

It has been confirmed by the present invention that, the compound, 2,2',4,4'-tetrahydroxy-3-(2"-hydroxy-3"-methylbutyl-3"-alkenyl)chalcone, has a high free radical scavenging capacity and exhibits an $IC_{50}$ value of 21.6 μM against DPPH radicals, indicating that the compound of the present invention, 2,2',4,4'-tetrahydroxy-3-(2"-hydroxy-3"-methylbutyl-3"-alkenyl)chalcone, has an excellent antioxidant activity, and thus can be used to prepare antioxidant skin care products, medicines or health products.

Compared with the prior art, the present invention has the following advantages:

The present invention realizes the preparation of a compound 2,2',4,4'-tetrahydroxy-3-(2"-hydroxy-3"-methylbutyl-3"-alkenyl)chalcone by isolating the compound from Morus alba leaves, with a yield of 10 to 120 mg/kg (and a purity of 85% to 95%). The present invention is of great significance for promoting the deep processing and utilization of Morus alba leaves, enhancing the added value of Morus alba leaves products, and promoting the sustainable development of the industry. Furthermore, the invention also provides a novel method for preparing 2,2',4,4'-tetrahydroxy-3-(2"-hydroxy-3"-methylbutyl-3"-alkenyl)chalcone.

DETAILED DESCRIPTION OF THE EMBODIMENTS

The following embodiments are further illustrations of the present invention, but not limitation of the present invention.

Embodiment 1

1. Preparation and Isolation of 2,2',4,4'-tetrahydroxy-3-(2"-hydroxy-3"-methylbutyl-3"-alkenyl)chalcone (1) Materials: Fresh Morus alba leaves were collected and washed with water.

(2) Drying and pulverizing: The *Morus alba* leaves were dried in the sun or in an oven, and then pulverized into powders with a pulverizer.

(3) Extraction: An aqueous solution of methanol (40% v/v) was added to the *Morus alba* leave powders according to a proportion of 5 mL/g *Morus alba* leaf powders (i.e., 5 mL of the aqueous solution of methanol was used for one gram of the *Morus alba* leaf powders) to allow extraction at 25° C. for 1 hour. The mixture was then subjected to a filtration process and the filtrate was collected.

(4) Organic solvent fractionation: The filtrate was concentrated at 40° C. to remove methanol and give a concentrated solution, followed by the addition of water having the same volume of the concentrated solution. The resulting solution was then successively subjected to extraction with petroleum ether (having the same volume of the resulting solution) for three times and with ethyl acetate (having the same volume of the resulting solution) for three times. The ethyl acetate extracts were concentrated to give a paste which would be subjected to subsequent purification.

(5) The paste, obtained by concentrating the ethyl acetate extracts, was chromatographed over a silica gel column (100-200 mesh) by gradient elution using chloroform-methanol with a volume ratio of 100/0 to 60/40, and an eluate was collected where the volume ratio of chloroform-methanol was 95/5. The eluate was then chromatographed over a C18 reversed-phase column by gradient elution using methanol-water with a volume ratio of 10/90 to 100/0, and an eluate was collected where the volume ratio of methanol-water was 60/40. The eluate was then dried by evaporation concentration at 60° C. to give a compound 1 (2,2',4,4'-tetrahydroxy-3-(2"-hydroxy-3"-methylbutyl-3"-alkenyl)chalcone).

By using this method, a yield of the compound 2,2',4,4'-tetrahydroxy-3-(2"-hydroxy-3"-methylbutyl-3"-alkenyl)chalcone was 10 to 40 mg/kg, with a purity of 8500 to 9500.

2. Structure Identification of the Compound 1

The compound 1 was easily soluble in methanol. Mass spectrometry results showed that the molecular weight of this compound was 564. $^1$H NMR (500 MHz, CD$_3$OD) and $^{13}$C NMR (125 MHz, CD$_3$OD) data were as listed in Table 1.

TABLE 1

$^{13}$C and $^3$H chemical shifts of compound 1

| Position | $^1$H | $^{13}$C |
|---|---|---|
| 1 | | 115.8 |
| 2 | | 163.2 |
| 3 | 6.33 | 103.8 |
| 4 | | 163.1 |
| 5 | 6.35 | 109.3 |
| 6 | 7.50 | 132.5 |
| 1' | | 114.3 |
| 2' | | 165.7 |
| 3' | | 118.1 |
| 4' | | 160.9 |
| 5' | 6.40 | 109.4 |
| 6' | 7.77 | 131.0 |
| 1" | 2.88, 3.05 | 30.2 |
| 2" | 4.37 | 77.0 |
| 3" | | 149.1 |
| 4" | 4.71, 4.82 | 110.9 |
| 5" | 1.83 | 18.1 |
| α | 7.71 | 118.0 |
| β | 8.07 | 141.8 |
| Carbonyl group | | 194.6 |

In view of the above, the compound 1 was identified to have a structure according to formula (I) and named as 2,2',4,4'-tetrahydroxy-3-(2"-hydroxy-3"-methylbutyl-3"-alkenyl)chalcone, easily soluble in methanol.

Formula (I)

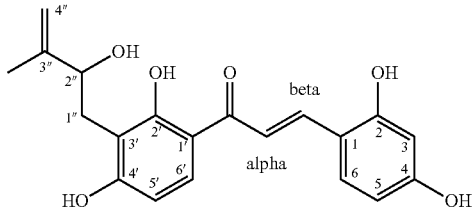

Embodiment 2

(1) Materials: Fresh *Morus alba* leaves were collected and washed with water.

(2) Drying and pulverizing: The *Morus alba* leaves were dried in the sun or in an oven, and then pulverized into powders with a pulverizer.

(3) Extraction: An aqueous solution of methanol (100% v/v, i.e., pure methanol) was added to the *Morus alba* leave powders according to a proportion of 20 mL/g *Morus alba* leaf powders (i.e., 20 mL of the aqueous solution of methanol was used for one gram of the *Morus alba* leaf powders) to allow extraction at 80° C. for 72 hours. The mixture was then subjected to a filtration process and the filtrate was collected.

(4) Organic solvent fractionation: The filtrate was concentrated at 60° C. to remove methanol and give a concentrated solution, followed by the addition of water having a volume five times that of the concentrated solution. The resulting solution was then successively subjected to extraction with petroleum ether (having the same volume of the resulting solution) for twelve times and with ethyl acetate (having the same volume of the resulting solution) for twelve times. The ethyl acetate extracts were concentrated to give a paste which would be subjected to subsequent purification.

The purification step was identical to that in the embodiment 1 to give the compound 1 which was identified to be 2,2',4,4'-tetrahydroxy-3-(2"-hydroxy-3"-methylbutyl-3"-alkenyl)chalcone.

By using this method, a yield of the compound 2,2',4,4'-tetrahydroxy-3-(2"-hydroxy-3"-methylbutyl-3"-alkenyl)chalcone was 70 to 120 mg/kg, with a purity of 85% to 95%.

Embodiment 3

(1) Materials: Fresh *Morus alba* leaves were collected and washed with water.

(2) Drying and pulverizing: The *Morus alba* leaves were dried in the sun or in an oven, and then pulverized into powders with a pulverizer.

(3) Extraction: An aqueous solution of ethanol (40% v/v) was added to the *Morus alba* leave powders according to a proportion of 20 mL/g *Morus alba* leaf powders (i.e., 20 mL of the aqueous solution of ethanol was used for one gram of the *Morus alba* leaf powders) to allow extraction at 55° C. for 24 hours. The mixture was then subjected to a filtration process and the filtrate was collected.

(4) Organic solvent fractionation: The filtrate was concentrated at 60° C. to remove ethanol and give a concentrated solution, followed by the addition of water having a volume three times that of the concentrated solution. The resulting solution was then successively subjected to extraction with petroleum ether (having the same volume of the resulting solution) for six times and with ethyl acetate (having the same volume of the resulting solution) for six times. The ethyl acetate extracts were concentrated to give a paste which would be subjected to subsequent purification.

The purification step was identical to that in the embodiment 1 to give the compound 1 which was identified to be 2,2',4,4'-tetrahydroxy-3-(2"-hydroxy-3"-methylbutyl-3"-alkenyl)chalcone.

By using this method, a yield of the compound 2,2',4,4'-tetrahydroxy-3-(2"-hydroxy-3"-methylbutyl-3"-alkenyl)chalcone was 30 to 80 mg/kg, with a purity of 85% to 95%.

Embodiment 4

(1) Materials: Fresh *Morus alba* leaves were collected and washed with water.

(2) Drying and pulverizing: The *Morus alba* leaves were dried in the sun or in an oven, and then pulverized into powders with a pulverizer.

(3) Extraction: An aqueous solution of ethanol (100% v/v, i.e., pure ethanol) was added to the *Morus alba* leave powders according to a proportion of 5 mL/g *Morus alba* leaf powders (i.e., 5 mL of the aqueous solution of ethanol was used for one gram of the *Morus alba* leaf powders) to allow extraction at 80° C. for 48 hours. The mixture was then subjected to a filtration process and the filtrate was collected.

(4) Organic solvent fractionation: The filtrate was concentrated at 80° C. to remove ethanol and give a concentrated solution, followed by the addition of water having the same volume of the concentrated solution. The resulting solution was then successively subjected to extraction with petroleum ether (having the same volume of the resulting solution) for six times and with ethyl acetate (having the same volume of the resulting solution) for six times. The ethyl acetate extracts were concentrated to give a paste which would be subjected to subsequent purification.

The purification step was identical to that in the embodiment 1 to give the compound 1 which was identified to be 2,2',4,4'-tetrahydroxy-3-(2"-hydroxy-3"-methylbutyl-3"-alkenyl)chalcone.

By using this method, a yield of the compound 2,2',4,4'-tetrahydroxy-3-(2"-hydroxy-3"-methylbutyl-3"-alkenyl)chalcone was 50 to 100 mg/kg, with a purity of 85% to 95%.

Embodiment 5

DPPH is a stable free radical. When a free radical scavenger is present, light absorption of DPPH will be reduced when the single electron is scavenged, which allows to evaluate free radical scavenging ability of the substance and accordingly determine antioxidant ability thereof. The DPPH radical scavenging ability of the compound 2,2',4,4'-tetrahydroxy-3-(2"-hydroxy-3"-methylbutyl-3"-alkenyl)chalcone was measured through the DPPH radical scavenging assay, so as to evaluate the antioxidant ability of the compound. The assay comprised the following steps:

1,1-Diphenyl-2-picrylhydrazyl (DPPH) was dissolved in absolute ethanol to obtain a solution with a concentration of 0.2 mM. The compound 2,2',4,4'-tetrahydroxy-3-(2"-hydroxy-3"-methylbutyl-3"-alkenyl)chalcone was dissolved in absolute ethanol. 80 µL of the ethanol solution of 2,2',4,4'-tetrahydroxy-3-(2"-hydroxy-3"-methylbutyl-3"-alkenyl) chalcone and 160 µL of the 0.2 mM DPPH ethanol solution were mixed and the mixture was placed in dark at room temperature for 30 minutes. Then, light absorbance at 517 nm was measured using a microplate reader (SpectraMax 190, Molecular Devices, USA). Results showed that, the compound had an $IC_{50}$ value of 21.6 µM against DPPH radicals, indicating that the compound of the present invention, 2,2',4,4'-tetrahydroxy-3-(2"-hydroxy-3"-methylbutyl-3"-alkenyl)chalcone, had an excellent antioxidant ability, and thus could be used to prepare antioxidant skin care products, medicines or health products.

The above descriptions are only preferred embodiments of the present invention. It should be noted that the above preferred embodiments should not be regarded as a limitation to the present invention, and the scope of the present invention shall be defined by the claims. For those of ordinary skill in the art, without departing from the spirit and scope of the present invention, several improvements and modifications can be made, which should also be within the scope of the present invention.

What is claimed is:

1. A method for preparing 2,2',4,4'-Tetrahydroxy-3-(2"-hydroxy-3"-methylbutyl-3"-alkenyl)chalcone, comprising: isolating the 2,2',4,4'-Tetrahydroxy-3-(2"-hydroxy-3"-methylbutyl-3"-alkenyl)chalcone from a *Morus alba* leaf, wherein, the 2,2',4,4'-Tetrahydroxy-3-(2"-hydroxy-3"-methylbutyl-3"-alkenyl)chalcone has a structure according to formula (I):

formula (I)

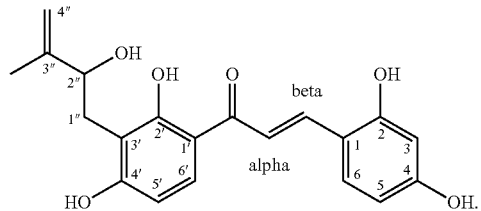

2. The method according to claim 1, wherein, the step of isolating the 2,2',4,4'-Tetrahydroxy-3-(2"-hydroxy-3"-methylbutyl-3"-alkenyl)chalcone from the *Morus alba* leaf comprises the following steps:

subjecting the *Morus alba* leaf to a first extraction with an aqueous solution of methanol or ethanol having a volume fraction of 40%-100% to obtain an extract, concentrating the extract to remove the methanol or ethanol to obtain a concentrated extract and dissolving the concentrated extract in water to obtain a dissolved extract, subjecting the dissolved extract to a second extraction with petroleum ether and ethyl acetate successively to obtain an ethyl acetate extract, and concentrating the ethyl acetate extract to obtain a paste;

chromatographing the paste over a silica gel column by a first gradient elution using chloroform-methanol with a volume ratio ranging from 100/0 to 60/40, collecting a first eluate wherein the volume ratio of chloroform-methanol is 95/5;

chromatographing the first eluate over a reversed-phase column by a second gradient elution using methanol-water with a volume ratio ranging from 10/90 to 100/0, collecting an second eluate wherein the volume ratio of methanol-water is 60/40 to obtain the 2,2',4,4'-Tetrahydroxy-3-(2"-hydroxy-3"-methylbutyl-3"-alkenyl) chalcone.

3. The method according to claim 2, wherein, the *Morus alba* leaf is provided as *Morus alba* leaf powders, and the *Morus alba* leaf powders are obtained by drying a fresh *Morus alba* leaf and pulverizing into powders.

4. The method according to claim 2, wherein, in the step of subjecting the *Morus alba* leaf to the first extraction with the aqueous solution of the methanol or ethanol having the volume fraction of 40%-100%, the aqueous solution of methanol or ethanol is used according to a proportion of 5 to 20 mL/g based on the *Morus alba* leaf, an extraction temperature of the first extraction ranges from 25° C. to 80° C., and an extraction time of the first extraction ranges from 1 hour to 72 hours.

5. The method according to claim 2, wherein, in the step of concentrating the extract to remove the methanol or ethanol to obtain the concentrated extract and dissolving the concentrated extract in the water, the extract is concentrated at 40° C. to 80° C. to remove the methanol or ethanol, and the concentrated extract is dissolved by adding the water wherein a volume of the water is 1 to 5 times the concentrated extract.

6. The method according to claim 2, wherein, in the step of subjecting the dissolved extract to the second extraction with the petroleum ether and the ethyl acetate successively to obtain the ethyl acetate extract, the second extraction is performed first with the petroleum ether for 3 to 12 times and then with the ethyl acetate for 3 to 12 times.

* * * * *